(12) United States Patent
Graf et al.

(10) Patent No.: US 10,197,435 B2
(45) Date of Patent: Feb. 5, 2019

(54) BALANCE FOR CALIBRATING PIPETTES

(71) Applicant: Sartorius Lab Instruments GmbH & Co. KG, Goettingen (DE)

(72) Inventors: Winfried Graf, Niemetal (DE); Christian Elo, Berlin (DE)

(73) Assignee: SARTORIUS LAB INSTRUMENTS GMBH & CO. KG, Goettingen (DE)

( * ) Notice: Subject to any disclaimer, the term of this patent is extended or adjusted under 35 U.S.C. 154(b) by 240 days.

(21) Appl. No.: 15/149,919

(22) Filed: May 9, 2016

(65) Prior Publication Data
US 2016/0250628 A1 Sep. 1, 2016

Related U.S. Application Data

(63) Continuation of application No. PCT/EP2014/002852, filed on Oct. 22, 2014.

(30) Foreign Application Priority Data

Nov. 8, 2013 (DE) .................. 10 2013 018 767
Feb. 7, 2014 (DE) .................. 10 2014 101 566

(51) Int. Cl.
*G01F 25/00* (2006.01)
*G01G 23/01* (2006.01)
(Continued)

(52) U.S. Cl.
CPC .............. *G01G 23/01* (2013.01); *B01L 3/021* (2013.01); *G01G 17/04* (2013.01); *G01G 19/303* (2013.01);
(Continued)

(58) Field of Classification Search
CPC ...... G01G 23/01; G01G 17/04; G01G 21/286; G01G 23/48; G01G 19/303; G01G 21/22;
(Continued)

(56) References Cited

U.S. PATENT DOCUMENTS

| 4,858,161 A | 8/1989 | Baumann |
| 6,615,638 B1 | 9/2003 | Lochner et al. |
| 2010/0288566 A1 | 11/2010 | Luchinger et al. |

FOREIGN PATENT DOCUMENTS

| DE | 3714540 C2 | 8/1996 |
| DE | 29912867 U1 | 3/2000 |

(Continued)

OTHER PUBLICATIONS

International Search Report in counterpart International Application No. PCT/EP2014/002852, dated Dec. 15, 2014.
(Continued)

*Primary Examiner* — Robert R Raevis
(74) *Attorney, Agent, or Firm* — Edell, Shapiro & Finnan, LLC

(57) ABSTRACT

A balance including a weighing chamber (16); a draft shield (23), which surrounds the weighing chamber; a climate module (34), which is detachably disposed in the weighing chamber; a processor (32), which is programmed to provide an evaporation rate correction value; a data input unit; and a data transmission path, over which data is exchanged between the climate module and the processor. Also disclosed are a climate module configured to electrically yet detachably couple to a balance, wherein the climate module forms a self-contained modular unit and includes various sensors (52, 54, 62) and a path over which data is transmitted to an external processor, and to a method for calibrating a pipette using a balance, wherein an evaporation rate is determined during the calibration process, and the measurement is corrected in accordance with the determined evaporation rate.

12 Claims, 4 Drawing Sheets

(51) Int. Cl.
*G01G 17/04* (2006.01)
*G01G 21/28* (2006.01)
*G01G 23/48* (2006.01)
*B01L 3/02* (2006.01)
*G01G 19/30* (2006.01)
*G05D 11/00* (2006.01)
*G01G 21/22* (2006.01)
*G01N 9/26* (2006.01)

(52) U.S. Cl.
CPC ............ *G01G 21/22* (2013.01); *G01G 21/286* (2013.01); *G01G 23/48* (2013.01); *G01N 9/26* (2013.01); *G05D 11/00* (2013.01)

(58) Field of Classification Search
CPC .......... B01L 3/021; G05D 11/00; G01N 9/26; G01F 25/0092
USPC ................. 73/1.74, 1.08; 177/2, 50, 264
See application file for complete search history.

(56) References Cited

FOREIGN PATENT DOCUMENTS

| EP | 1092473 A2 | 4/2001 |
|---|---|---|
| EP | 1975577 A1 | 10/2008 |
| EP | 2251657 A1 | 11/2010 |

OTHER PUBLICATIONS

International Preliminary Report on Patentability in counterpart International Application No. PCT/US2014/002852, dated May 12, 2016, 8 pages.

BALANCE FOR CALIBRATING PIPETTES

CROSS REFERENCE TO RELATED APPLICATIONS

This is a Continuation of International Application PCT/EP2014/002852, which has an international filing date of Oct. 22, 2014, and the disclosure of which is incorporated in its entirety into the present Continuation by reference. The following disclosure is also based on and claims the benefit of and priority under 35 U.S.C. § 119(a) to German Patent Application Nos. DE 10 2013 018 767.2, filed Nov. 8, 2013, and to DE 10 2014 101 566.5, filed Feb. 7, 2014, which are also incorporated in their respective entireties into the present Continuation by reference.

FIELD OF THE INVENTION

The invention relates to a balance, which is used to calibrate pipettes, and a method for calibrating a pipette.

BACKGROUND

For the gravimetric calibration of pipettes high resolution precision balances, analytical balances, semi micro balances, micro balances or ultra micro balances (hereinafter referred to as balances) are used. When conducting the gravimetric calibration of the nominal volume of pipettes with the aid of a balance, a volume of liquid that is to be determined is dispensed from the pipette tip into a weighing vessel; and the weighing value is used to determine the volume of the quantity of liquid that was dispensed. In this respect it is known to consider additional parameters, such as the air temperature, the liquid density, the air humidity and the air pressure, since these parameters affect the weighing result. For example, the air temperature and the air humidity have an effect on the evaporation rate of the sample liquid.

According to standard operating procedures, volumes of up to 1 µl are calibrated. Especially with very small volumes the effect of the liquid evaporation (and, as a result, the error) on the weighing result and on the accuracy of the calibration of the pipette should not be considered to be negligible.

In order to minimize the evaporation of the sample liquid during the weighing operation, so-called evaporation traps, which are disposed in the weighing chamber, are used in the application of a pipette calibration process. These evaporation traps are filled with water; and the evaporation of this water causes the air volume in the weighing chamber to be highly saturated with water. As a result, it is possible to achieve a relative air humidity of up to 90%.

Nevertheless, even with the use of evaporation traps, it cannot be completely prevented that a portion of the sample liquid will evaporate during the calibration process. This is due to the fact that the pipetting operation itself leads to air movements and to an air exchange between the weighing chamber and the surrounding area, so that the saturation of the air volume fluctuates.

In addition, when using a balance, a valid measurement value cannot be obtained immediately after the pipette to be calibrated has dispensed a specified volume of liquid; instead, it is necessary to wait a certain amount of time. With respect to falsification due to the evaporation this time period should be less than 60 seconds. Experience shows that, depending on the resolution, the handling and the type of balance, the amount of time is in a magnitude of 5 to 20 seconds. It cannot be prevented that during this process time a portion of the liquid to be measured has already evaporated, and, as a result, the measurement result is falsified. This effect disproportionately affects small volumes.

Therefore, it is known in the prior art that the weighing value is corrected using an assumed rate of evaporation. Such evaporation rates have been determined experimentally for specific vessel geometries and values of the relative humidity inside the weighing chamber and range, for example, from 0.05 µg/s, when pipetting into a narrow neck flask using an evaporation trap that guarantees a relative humidity of 90% in a closed weighing chamber, to, for example, 4.6 µg/s, when pipetting into a beaker, again using an evaporation trap, which however, generates a relative humidity of less than 90% in an open weighing chamber. These values apply to distilled or deionized water of quality 3 in accordance with ISO 3696 as the pipetting liquid. For the calibration of pipettes a fixed value for the evaporation is generally assumed.

It is easy to see that the effect of the evaporation on the measurement error cannot be considered to be negligible. At an assumed evaporation rate of 0.26 µg/s, the result is an evaporation volume of 3.12 µl during a process period of 12 seconds for handling and settling the balance. The standard measurement uncertainty, according to EN-ISO 8655-6, in a measurement range of 1 µl to 10 µl is 2 µl. Therefore, the assumed evaporation is greater than the measurement error. In this case the assumed rate of evaporation of 0.26 µg/s is still a rather low value; to some extent significantly higher values have been mentioned in the literature.

In order to reduce the effect of the environment on the accuracy of the measurement, the prior art discloses a number of measures for determining the mass.

For mass comparators it is known, for example, that the air buoyancy is determined by a comparison measurement of two reference objects having a mass and density that are already known beforehand.

It is known that the temperature, the air pressure and the humidity also affect the balance itself. For this reason, in order to compensate for the variances in the weighing result with changing ambient parameters, correction factors are stored in the device, for example, in the form of curves or tables. In addition, temperature and air humidity sensors are disposed in the surrounding area of the load cell, for example, in the laboratory. Then these temperature and air humidity sensors are used to automatically correct the balance itself, as a function of the changing ambient conditions.

The European patent EP 1 975 577 A1 discloses a balance for gravimetric calibration of pipettes, which has a draft shield and a built-in temperature sensor, air pressure sensor and air humidity sensor.

The German patent DE 37 14 540 C2 describes a method for automatically calibrating a high resolution electronic balance, wherein such environmental factors as the temperature change and the humidity change, both of which are detected from the outside, are used to calibrate the balance itself. The corresponding calibration factor is determined by a computer and corrects the weighing result.

The German patent DE 299 12 867 U1 discloses an analytical balance with a measuring sensor for ambient parameters. In this case the analytical balance has a display that is provided on the rear wall of the weighing chamber. The display shows the temperature in the weighing chamber and the air humidity in the weighing chamber as well as, in general, the air pressure that is usually present. In this case it is assumed that, when the air is wet, the surface of the sample to be weighed will be covered with moisture, which is a function of the variances in the air humidity. Therefore, the operator is informed by the display that, for example, with changing air humidity the sample to be weighed should remain in the weighing chamber longer, in order to obtain a stable end value of the surface moisture. If there are extreme fluctuations in the air pressure, the operator can perform a so-called buoyancy correction by feeding the displayed data to a processor in the balance via an input unit. With respect to the temperature, this temperature is used to determine the deviation from the reference temperature and to consider corresponding correction factors.

Finally there are also climatized measuring chambers, in which there are balances. In this case the climate data, which are determined by the sensors and which relate to the measuring chamber, are entered into specific software, which determines then the corresponding correction parameters, which are fed manually or automatically into the balance.

All of these measures in themselves do not lend themselves to increasing the measuring accuracy when calibrating pipettes, because in the best case scenario the sensors are placed in the immediate vicinity of the balance, but not on or in the balance itself.

SUMMARY

An object of the present invention is to provide a balance that is compact and that ensures with less complexity a higher measuring accuracy when calibrating pipettes.

This object, according to one formulation of the invention, is achieved with a balance, comprising a weighing chamber; a draft shield, which surrounds the weighing chamber; a climate module, which includes an air pressure sensor, an air humidity sensor and an air temperature sensor and which is disposed in the weighing chamber in such a way that it can be removed; a processor which provides an evaporation rate correction factor, for example, by reading out of an evaporation rate correction table or by computation; a data input unit; and a data transmission path, over which data can be exchanged between the climate module and the processor. The object, according to a further formulation, is achieved with a climate module configured to electrically couple to a balance in a detachable manner, wherein the climate module forms a self-contained modular unit and comprises an air pressure sensor, an air humidity sensor and an air temperature sensor, as well as a data transmission path, over which data can be sent to a processor external to the climate module.

The invention makes use of the idea of increasing the accuracy of the calibration process by providing, on the one hand, those climate values which affect the weighing result of the balance via the climate module. This feature permits the weighing result to be suitably corrected directly in the balance. On the other hand, the balance itself can use the climate values to determine a more realistic evaporation rate, on which the correction of the weighing result is based, inside the draft shield. Then there is no need to work with a predefined, assumed rate of evaporation, but rather it is possible to work with an individual rate of evaporation that has been determined in real time and that in terms of the actual ambient conditions inside the draft shield can be modified, starting from a predefined assumption, or can even be determined all over again.

Furthermore, there is the advantage that all of the components and functions, which are necessary for correcting the weighing results, are combined in the balance. Therefore, no external computers, sensors, etc. are necessary. Instead, the user can be provided with a compact measurement laboratory, which can be designed so that it is even portable. Since the climate module is interchangeable (i.e., can be detached from the balance without destroying it), it can be sent, if desired, to an external institute or service provider for calibration. In the meantime the balance can still be used by installing a replacement climate module. As a result, it is possible to have on a rolling basis one or (in the case of several balances) a plurality of climate modules being calibrated, while measuring with the other climate modules.

The climate module offers an additional advantage that older balances can be retrofitted. The only requirement for such a retrofitting is, in addition to the data transmission path, the software of the processor.

In terms of accuracy the balance of the invention has the advantage that the climate data are measured behind the draft shield (and not just in the chamber, in which the balance is located). In addition, since the climate values are transmitted automatically to the processor, transmission errors can be virtually eliminated. According to the German patent DE 299 12 867 U1, such transmission errors are possible, for example, when transferring values from the so-called calibration certificate into the calibration software.

According to one embodiment, it is provided that the climate module is connected to the processor via an electrical plug-in connection or a wireless transmission. In the case of a plug-in connection, it can be integrated into a mechanical receptacle, which is used to attach the climate module to the balance. In this way the data transmission path to the processor is automatically established, when the climate module is installed inside the draft shield. In the case of a wireless transmission the climate module can be disposed at any location inside the draft shield, for example, on a side wall, where it will interfere the least, without having to take into consideration whether a plug-in connection can be arranged at this location in such a way that it is useful. In addition, the absence of a plug-in connection has the advantageous effect that the interior of the weighing compartment can be designed to be smoother and, therefore, easier to clean.

In addition, it can be provided that there is a sensor for determining the degree of ionization in the weighing chamber; and this sensor is coupled to the data transmission path. As a result, an additional parameter can be determined and taken into account in the correction of the weighing result. The processor generates, as a function of the degree of ionization that is determined, an output signal. Furthermore, the display of such an output signal can also indicate to the user that the degree of ionization inside the weighing chamber is too high and that appropriate steps should be taken to remedy it.

It can also be provided that the weighing chamber has a light sensor, which is coupled to the data transmission path. Such an arrangement allows another parameter to be determined and taken into account in correcting the weighing result. The processor can output an output signal following a specified level of incident light. As a result, it is possible to determine the effect of the incident light on the weighing process, so that appropriate steps can be taken in the process itself. The output signal can also be an indicator.

According to one embodiment, it can be provided that the processor is designed such that it determines the rate of evaporation of at least the sample liquid, based on the air density and the air temperature in the weighing chamber. This arrangement makes it possible to receive from the climate module the metrologically traceable values in sync with the download of the mass value, with which the processor is able to correct the weighing result for the gravimetric calibration of the nominal volume of a pipette.

Preferably an evaporation trap or moisture trap is disposed inside the draft shield. This arrangement allows the air humidity inside the draft shield to be moved to the maximum possible value, so that the rate of evaporation drops.

One embodiment provides an electronic memory, in particular, an EEPROM, which can be read out by an external reader and in which the calibration values and the correction values for the climate module can be stored. In order to make adjustments, the calibration values and the correction values can be stored in an electronic memory on the climate module, in particular, can be stored in an EEPROM. This is done at an external service provider. If the climate module is then reconnected to the balance, these data are then immediately available to the processor of the balance. In addition, the memory can be used to store, among other things, at least some of the following sensor calibration data: the number of the calibration certificate, the current calibration values, the calibration date, the name of the calibration laboratory, the name of the person in charge and the calibration history. In addition, the memory of the climate module can also be used to store so-called uncertainty values for each climate variable, so that, for example, in order to compute the rate of evaporation, the computation of the uncertainty of the evaporation rate can also be performed by the balance.

According to one embodiment, it is provided that the climate module can also be used as a stand-alone unit external to a balance and can be connected to a USB port of a PC via an I²C bus. This arrangement makes it easier to perform an external calibration. In addition, the climate module can be used in other applications to record climate variables without having to be connected to a balance. For this purpose the printed circuit board of the climate module can easily have a plug-in extension, in order to be connected to a USB adapter.

The object, according to yet another formulation of the invention, is achieved with a method for calibrating a pipette with the aid of a balance, wherein an evaporation rate is determined during the calibration process, and the measurement is corrected as a function of the evaporation rate that is determined. This approach significantly increases the measuring accuracy or, more specifically, the accuracy of the calibration process, because the calibration process is not just based on one predefined evaporation rate, which is assumed (more or less correctly), but rather on values that are close to real time conditions and that are a function of the current climate conditions during the calibration process.

According to one embodiment it can be provided that a predefined evaporation rate is selected as a function of the climate parameters that are provided by the climate module. They can be stored, for example, in a database inside the processor of the balance. In this embodiment the climate is adjusted virtually in groups; and an evaporation rate is selected as a function of the respective group (in one simplified example: low air humidity, medium air humidity, high air humidity); and this evaporation rate is used to determine a correction factor for the calibration process. At the same time the temperature can also flow into the computation, because it, too, has an effect on the evaporation rate.

According to an alternative embodiment it can be provided that an actual evaporation rate is computed as a function of the climate parameters that are provided by the climate module. In this embodiment an actual evaporation rate is determined by the processor using the actual climate values.

According to one embodiment it is provided that the climate values are recorded during the entire calibration process; and that the correction factor is modified based on the evaporation rate, in the event that the climate values change so much that it is deemed expedient to base the correction of the calibration process on a different evaporation rate. The result of this embodiment is an even greater increase in the accuracy, since this embodiment compensates for the influences that result from a change in the micro climate inside the draft shield during the calibration process.

BRIEF DESCRIPTION OF THE DRAWINGS

Additional features and advantages of the invention will become apparent from the following description and from the following drawings, to which reference is made. The drawings show in.

DETAILED DESCRIPTION

Figure 1:
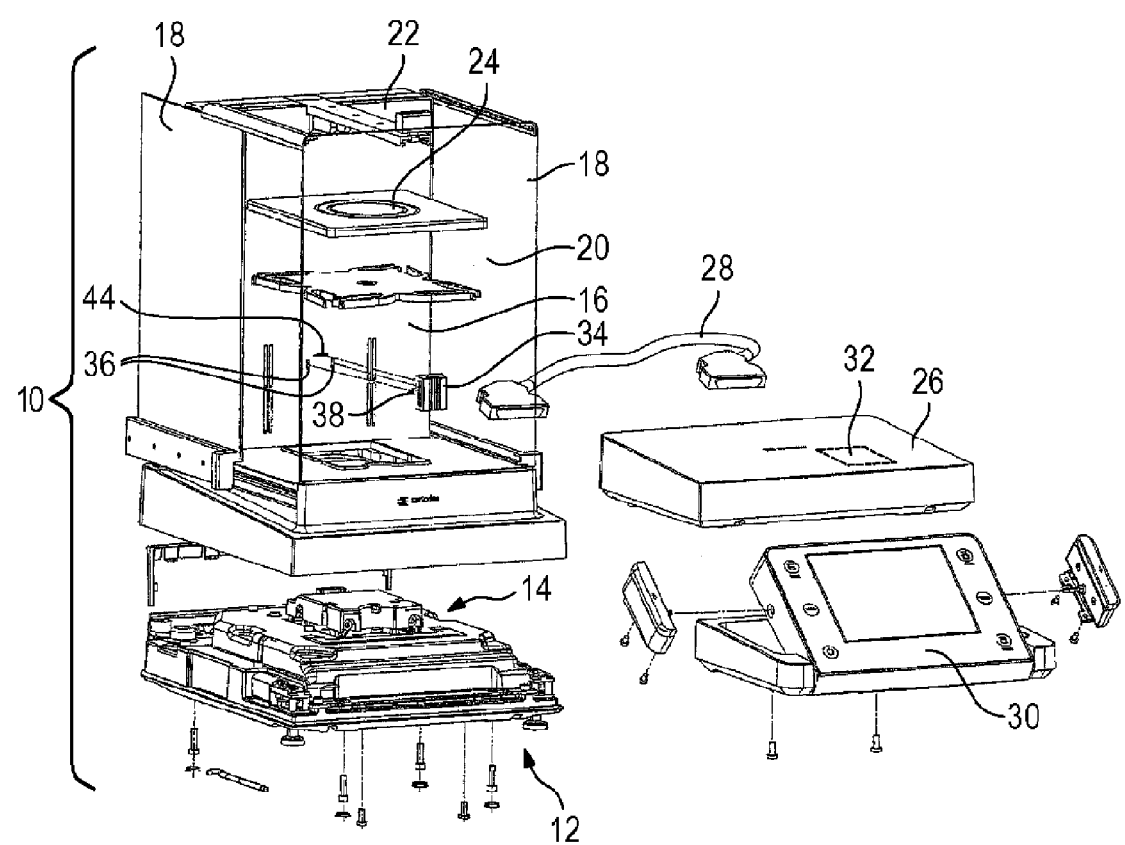
FIG. 1 an exploded view of a balance, according to the invention.

FIG. 1 shows a high resolution electronic balance (precision balance) that can be used during the calibration of pipettes.

The balance comprises a load cell 14 with a base 12. In addition, the load cell 14 comprises a weighing chamber 16, which is formed by a draft shield with adjustable side walls 18, a front wall 20 and a rear wall 22. The weighing chamber 16 is separated from the surrounding area with the draft shield. A weighing dish 24 is used to hold the sample to be weighed. These components together form a weighing module 10.

An electronic evaluation system 26, which is designed as a separate part in this embodiment, is electronically coupled to the load cell 14 via a cable 28. A display unit 30, which is coupled to the evaluation system 26, is used both as a display and as a data input unit. While the electronic evaluation system 26 and the display 30 are embodied as components physically separated from the weighing module 10 in the illustrated embodiment, other embodiments can incorporate one or both of these components 26 and 30 into the weighing module 10.

The electronic evaluation system 26 houses, among other things, a processor 32, which receives data from the load cell 14. Furthermore, this evaluation system also includes all of the electronic components that are necessary to operate the balance.

The weighing chamber 16 has a climate module 34, which is designed as a structurally separate unit and which can be mechanically coupled to the rear wall 22 through a disconnectable plug-in connection (hence, is attached in a manner allowing the climate module to be disconnected without destroying it), preferably without the aid of a tool.

For this purpose the rear wall 22 has two slots 36, which are spaced apart from each other and in which flexible locking hooks 38 (see also FIG. 2) engage with the outer housing 40 of the climate module.

Figure 2:
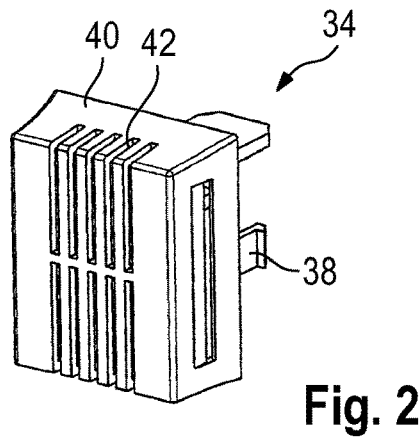
FIG. 2 a perspective view of an inventive climate module that can be used in the balance of the invention, FIG. 3 a side view of the climate module from FIG. 2 without the outer housing, FIG. 4 a plan view of the climate module from FIG. 2, also without the outer housing, FIG. 5 in schematic form an inventive balance that is provided with an evaporation trap.
Figure 3:
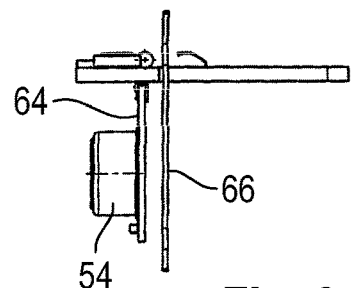
Figure 4:
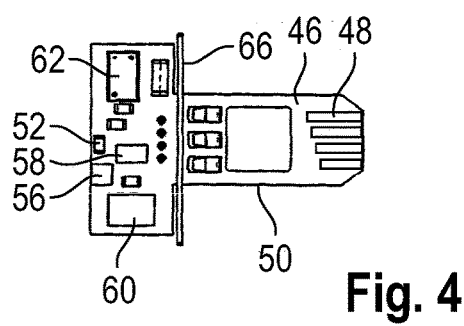

FIGS. 2 to 4 show the climate module 34 in more detail.

The outer housing 40 has a number of apertures 42, through which the interior of the outer housing 40 changes over into the weighing chamber 16 and becomes a part of the weighing chamber 16, so that the climate inside the weighing chamber 16 matches the climate inside the outer housing 40.

The climate module 34 is electronically coupled via an electrical plug-in connection to a corresponding plug receptacle 44 in the rear wall 22. The plug receptacle 44 is electrically connected to the processor 32. A plug 46 with contacts 48 is plugged into the plug receptacle 44 on the climate module 34. As a result, the plug 46 forms a module-sided part of the electrical plug-in connection.

As an alternative to an electrical plug-in connection, a wireless transmission, for example, WLAN or Bluetooth, can be used.

The electrical plug-in connection (or the wireless transmission used as an alternative) forms a data transmission path, over which the data can be transferred from the climate module 34 to the processor 32 and, if desired, can be transferred back to the climate module.

The plug 46 is preferably a section of a circuit board 50, on which a plurality of sensors for detecting the climate in the weighing chamber 16 are disposed. Therefore, an air temperature sensor 52, an air humidity sensor 54, a light sensor 56, which is arranged directly in the vicinity of an aperture 42, and a sensor 58 for detecting the degree of ionization in the weighing chamber 16 are provided on the circuit board 50, and an electronic memory 60 is also provided on the circuit board. An air pressure sensor 62 is mechanically and electrically coupled to the circuit board 50 with a bracket 64.

A plurality of the sensors can also be combined into combined sensors.

A wall 66 closes the shell-like outer housing 40, so that the narrow tongue-like section of the circuit board 50, which is located to the right of the wall 66 in FIG. 4, can be inserted into the rear wall 22 and the plug receptacle 44.

Each sensor is coupled to the processor 32 via corresponding contacts 48. Similarly the memory 60 is coupled to the processor 32.

Then a sample to be weighed is placed on the weighing dish 24, i.e., is dispensed by a pipette in such a way that it hits the weighing shell 24.

The air pressure, the air humidity and the air temperature are determined using the sensors 62, 54 and 52 respectively; and the corresponding data are transmitted to the processor 32.

In addition, the calibration values and the correction values for the climate module 34, which had been input during the calibration of the climate module, are stored in the memory 60.

This calibration is performed outside of the balance. To this end the climate module 34 is simply unplugged from the weighing chamber 16 without having to disconnect a wire connection. Then the climate module 34 is sent to an appropriate calibration institute that stores, for example, the number of the calibration certificate, the new calibration values, the calibration date, the name of the calibration laboratory, the name of the person in charge and the calibration history in the memory 60. These values are read out later by the application program, when the climate module 34 is once again in the balance, are completely or partially read out and flow directly into the computations.

Even the values of the light sensor 56 and the sensor 58 for determining the degree of ionization in the weighing chamber 16 are determined.

For example, when the level of incident light increases, a corresponding signal will be shown on the display that, for example, the measurement is uncertain due to increased exposure to sunlight and, thus, due to a temperature change in the weighing chamber. As a result, the processor sends an output signal as a function of the exposure to incident light.

The memory 60 is preferably an EEPROM.

In addition, the connection between the climate module 34 and the rest of the balance is implemented using an I$^2$C bus.

The climate module 34 can be connected to a computer using a USB adapter, into which the climate module is inserted, in order to calibrate the sensors 52 to 58 and 62 without having to connect the climate module 34 to the weighing module 10.

As can be seen, the climate module is designed in such a way that it can also be used as a stand-alone unit external to a balance and can be connected to a USB port of a PC using an I$^2$C bus.

An evaporation rate correction table is stored in the processor 32. In a simple embodiment this table can be stored as a table of values that allocates different evaporation rates to disparate climate conditions. In a more complex embodiment the evaporation rate correction table can also be configured as a characteristic map, in which each evaporation rate that is to be assumed is stored as a function of a plurality of climate parameters, for example, the temperature and the humidity. It is also conceivable that the evaporation rate correction table is stored in the form of a mathematical formula, with which the processor computes an actual evaporation rate, which is to be currently assumed, or an evaporation rate correction value, as a function of the respective current climate data.

How a pipette can be calibrated with the balance comprising the climate module will be explained below with reference to FIGS. 5 and 6.

Figure 5:
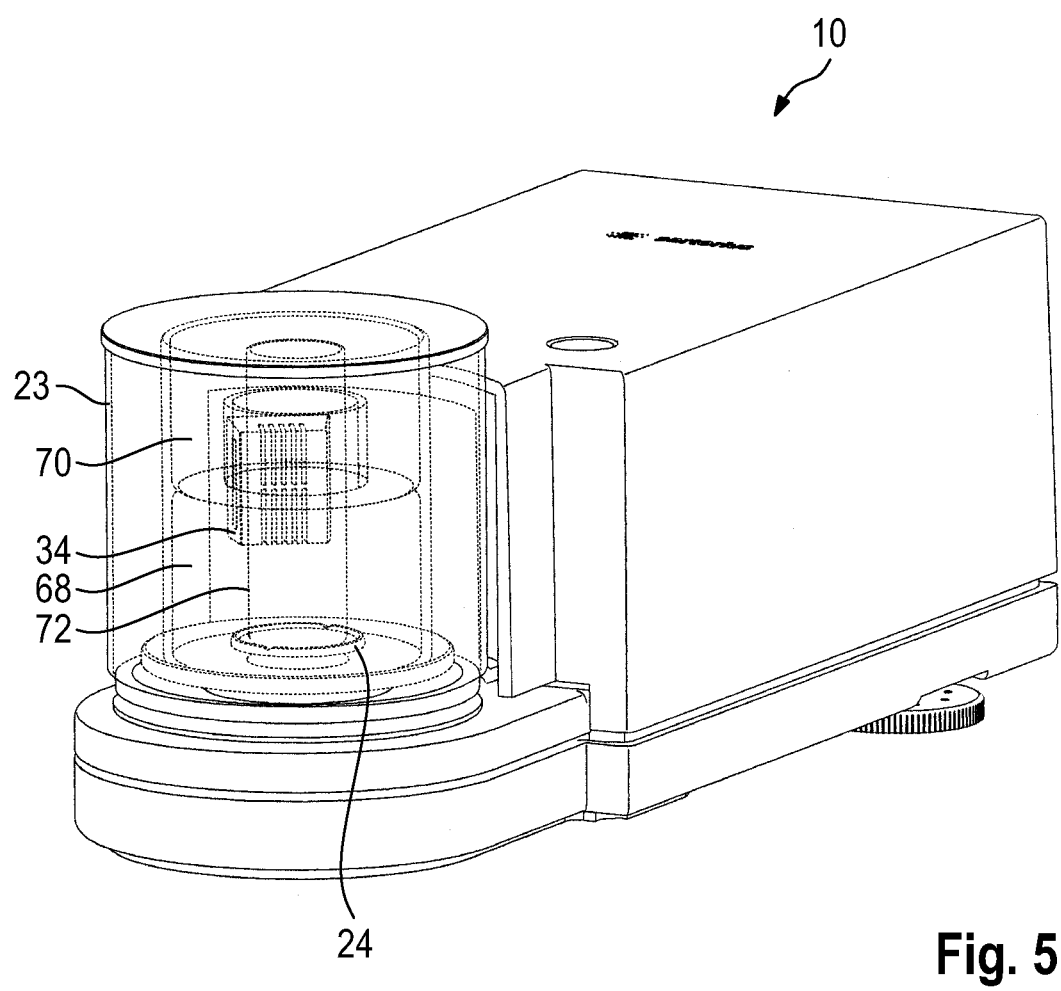

In the balance 10, shown in FIG. 5, an evaporation trap 68 is disposed inside a draft shield 23, which in this embodiment is designed cylindrical. This evaporation trap comprises a reservoir 70 for an evaporation liquid, for example, water. Inside the evaporation trap 68 there is a cylinder 72 that rests on the weighing dish 24 and that receives the liquid to be pipetted.

Figure 6:
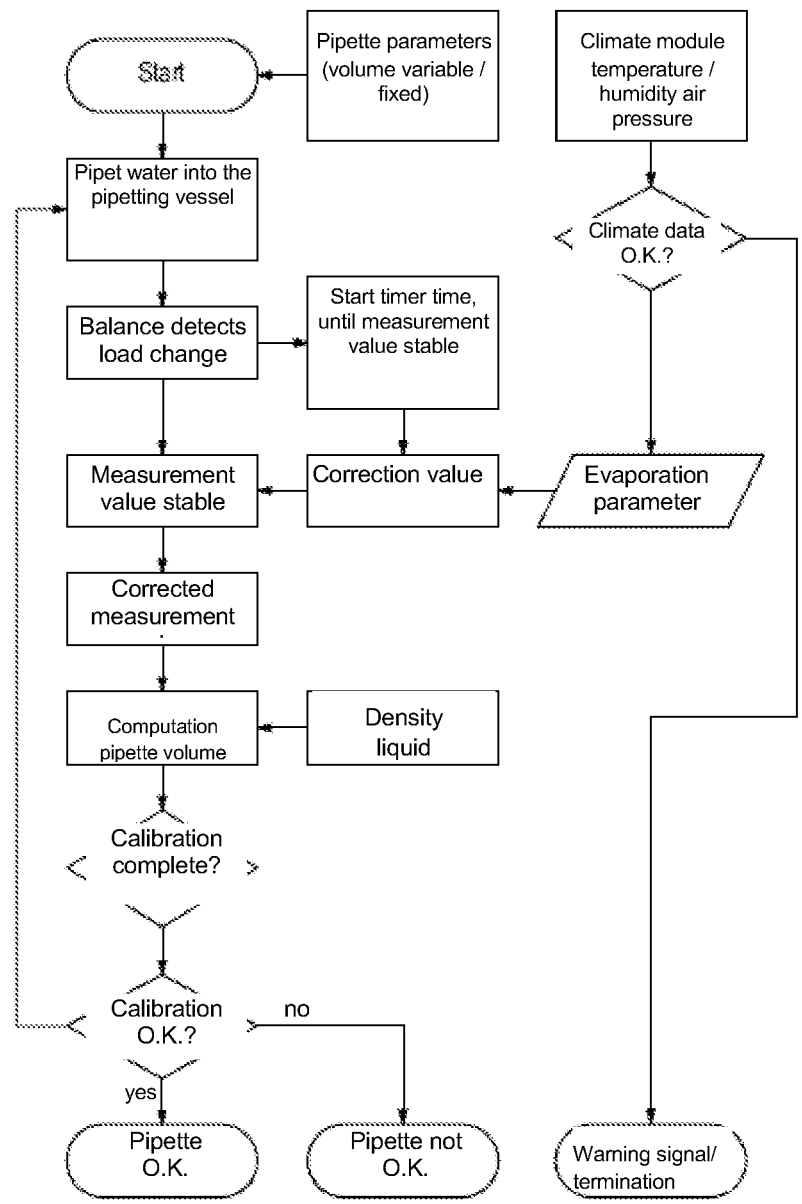
FIG. 6 a flow chart for calibrating a pipette using the method of the invention.

FIG. 6 is a flow chart that shows the calibration of the pipette with the correction of the effect of the evaporation.

At the start of the calibration process, the necessary pipette parameters, for example, the volume or also the calibration liquid that is used, can be entered, for example, the display unit 30, which cannot be seen in FIG. 5, of the balance, when the display unit is designed as a touch screen and, as a result, is used as a data input unit.

If at this point a liquid volume that is to be weighed is pipetted into the cylinder 72, the balance detects a load change that initiates the measuring process. At the same time the climate data can be extracted from the climate module 34. After prechecking whether these climate data are basically plausible, the processor 32 computes an assumed evaporation rate with the aid of the evaporation rate correction table. This assumed evaporation rate is used to correct the computed weighing value taking into consideration the evaporation of the pipetting liquid.

At the same time the processor 32, taking into consideration the climate parameters, can compute the way in which these climate parameters affect the weighing result independently of the evaporation rate, i.e., for example, the measurement uncertainty of the balance. The measurement uncertainty can be displayed or outputted through use of a protocol.

Such a corrected weighing result can be used to compute very precisely the volume of the pipette to be calibrated. In the event that after the current measurement the calibration is still not complete, an additional pipetting operation is required. Then the process of settling the balance and correcting the currently determined weighing result is repeated. During this correction, the climate that is actually present in real time is considered again. In the event that, for example, the humidity in the weighing chamber has changed between the first and the second measurement, a changed rate of evaporation is also considered. The result of such a procedure is a very high precision of measurement. Upon completion of this process, it is decided whether the pipette satisfies the respective requirements (in this case the pipette is rated as O.K.) or does not satisfy the respective requirements (in this case the pipette is rated as not O.K.); and more comprehensive measures, such as, for example, a repair, are initiated.

LIST OF REFERENCE NUMERALS 10 weighing module
12 base
14 load cell
16 weighing chamber
18 side wall
20 front wall
22 rear wall
23 draft shield
24 weighing dish
26 evaluation system
28 cable
30 display unit
32 processor
34 climate module
36 slots
38 locking hooks
40 outer housing
42 apertures
44 plug receptacle
46 plug
48 contacts
50 printed circuit board
52 air temperature sensor
54 air humidity sensor
56 light sensor
58 sensor
60 memory
62 air pressure sensor
64 bracket
66 wall
68 evaporation trap
70 reservoir
72 cylinder

What is claimed is:

1. Balance for calibrating pipettes, comprising:
a draft shield, which delimits a weighing chamber;
a climate module, which comprises an air pressure sensor, an air humidity sensor and an air temperature sensor, and which is configured to mount detachably within the weighing chamber and is configured to detach without damage from the weighing chamber;
a processor which is configured to receive signals from the air pressure, the air humidity, and the air temperature sensors and is programmed to provide an evaporation rate correction value in accordance with the air pressure, the air humidity, and the air temperature signals;
a data input unit; and
a data transmission path, over which data comprising the air pressure, the air humidity, and the air temperature signals is exchanged between the climate module and the processor.

2. The balance as claimed in claim 1, wherein the processor provides the evaporation rate correction value from an evaporation rate correction table or computes the evaporation rate correction value.

3. The balance as claimed in claim 1, wherein the data transmission path comprises an electrical plug-in connection.

4. The balance as claimed in claim 1, further comprising a sensor configured to determine a degree of ionization in the weighing chamber as a further signal exchanged between the climate module and the processor over the data transmission path.

5. The balance as claimed in claim 1, further comprising a light sensor arranged in the weighing chamber and configured to determine a light intensity in the weighing chamber, and to output an additional signal over the data transmission path.

6. The balance as claimed in claim 1, wherein the processor is programmed to determine a measurement uncertainty, based on climate parameters in the weighing chamber.

7. The balance as claimed in claim 1, further comprising an evaporation trap disposed inside the draft shield.

8. The balance as claimed in claim 1, wherein the data transmission path comprises a wireless transmission path.

9. Method for calibrating a pipette with a balance that comprises a draft shield that delimits a weighing chamber and separates the weighing chamber from a surrounding area, said method comprising:
mounting an air pressure sensor, an air humidity sensor, and an air temperature sensor within the weighing chamber, wherein the sensors are coupled to a processor for outputting a measurement,
determining an evaporation rate from calibration data during a calibration process, and
correcting the measurement as a function of the determined evaporation rate.

10. The method as claimed in claim 9, further comprising selecting one of a plurality of predefined evaporation rates as a function of climate parameters provided by the sensors.

11. The method as claimed in claim 9, further comprising computing an actual evaporation rate as a function of climate parameters provided by the sensors.

12. The method as claimed in claim 9, further comprising:
recording climate values throughout the calibration process; and
modifying the determined evaporation rate once the climate values change by a predetermined amount.

* * * * *